US009267001B2

(12) United States Patent
El Fray et al.

(10) Patent No.: US 9,267,001 B2
(45) Date of Patent: Feb. 23, 2016

(54) TELECHELIC MACROMER, METHOD FOR PRODUCING TELECHELIC MACROMER AND COMPOSITION CONTAINING TELECHELIC MACROMER

(71) Applicant: ZACHODNIOPOMORSKI UNIWERSYTET TECHNOLOGICZNY W SZCZECINIE, Szczecin (PL)

(72) Inventors: Miroslawa El Fray, Dobra (PL); Jedrzej Skrobot, Ilawa (PL)

(73) Assignee: ZACHODNIOPOMORSKI UNIWERSYTET TECHNOLOGICZNY W SZCZECINIE, Szczecin (PL)

( * ) Notice: Subject to any disclaimer, the term of this patent is extended or adjusted under 35 U.S.C. 154(b) by 442 days.

(21) Appl. No.: 13/727,859

(22) Filed: Dec. 27, 2012

(65) Prior Publication Data
US 2014/0187663 A1 Jul. 3, 2014

(51) Int. Cl.
*C08F 2/46* (2006.01)
*C08G 61/04* (2006.01)
*C08G 63/47* (2006.01)
*C07C 69/54* (2006.01)
*C07C 55/02* (2006.01)
*C07C 57/04* (2006.01)
*C08G 65/00* (2006.01)
*C07C 271/20* (2006.01)

(52) U.S. Cl.
CPC ............... *C08G 63/47* (2013.01); *C07C 55/02* (2013.01); *C07C 57/04* (2013.01); *C07C 69/54* (2013.01); *C07C 271/20* (2013.01); *C08G 65/00* (2013.01)

(58) Field of Classification Search
CPC .... C07C 271/22; C07C 67/10; C07C 69/602; C07C 269/06; C07C 69/734; C07C 271/20; C07C 55/02; C07C 57/04; C08G 63/47; C08G 65/00
USPC ..................... 522/90, 1, 113; 520/1
See application file for complete search history.

(56) References Cited

U.S. PATENT DOCUMENTS

| 4,919,151 | A | 4/1990 | Grubbs et al. | 128/898 |
|---|---|---|---|---|
| 5,290,217 | A | 3/1994 | Campos | 600/37 |
| 5,634,931 | A | 6/1997 | Kugel | 606/151 |
| 6,176,863 | B1 | 1/2001 | Kugel et al. | 606/151 |
| 6,747,088 | B1 | 6/2004 | Schwalm et al. | 524/507 |
| 2005/0202067 | A1 | 9/2005 | Lendlein et al. | 424/443 |
| 2008/0258345 | A1 | 10/2008 | Bens et al. | 264/401 |
| 2008/0318188 | A1 | 12/2008 | Stansbury et al. | 433/215 |
| 2009/0074868 | A1 | 3/2009 | Elisseeff et al. | 424/486 |
| 2009/0209717 | A1 | 8/2009 | Kelch et al. | 526/319 |
| 2009/0270999 | A1 | 10/2009 | Brown | 623/23.72 |
| 2009/0324666 | A1 | 12/2009 | Krongauz et al. | 424/409 |
| 2010/0179576 | A1 | 7/2010 | Halevy | 606/151 |
| 2011/0021695 | A1 | 1/2011 | Akiyama et al. | 524/590 |
| 2011/0184407 | A1 | 7/2011 | Craig | 606/41 |

FOREIGN PATENT DOCUMENTS

| WO | WO 99/19003 | 4/1999 | ............. A61L 25/00 |
|---|---|---|---|
| WO | WO 2005/055958 A2 | 6/2005 | |

OTHER PUBLICATIONS

El Fray, Miroslawa et al, Synthesis and characterization of telechelic macromers containing fatty anci derivatives, Jul. 31, 2012, Reactive & Functional Polymers, 72, 781-790.*
Office Action mailed Aug. 8, 2014 in corresponding U.S. Appl. No. 13/727,876.
Response as filed Oct. 6, 2014 in corresponding U.S. Appl. No. 13/727,876.
Office Action mailed Feb. 10, 2015 in corresponding U.S. Appl. No. 13/727,876.
Response as filed Mar. 31, 2015 in corresponding U.S. Appl. No. 13/727,876.
*Synthesis and preliminary crosslinking studies of new photocurable poly(ester-urethane)s for biomedical applications*; Skrobot et al.; Chemical Abstracts Service, Columbus, Ohio; Polish Jourlan of Applied Chemistry; vol. 53, No. 2; 2009; pp. 175-180; Database accession No. 154:268423.
*Photosensitive injectable systems for biomedical applications*; Skrobot et al.; Polimery, Instytyt Chemii Przemysowej, Warsaw, PL; vol. 55, No. 4; Jan. 2020; pp. 267-276.
*Review: Photopolymerizable and Degradable Biomaterials for Tissue Engineering Applications*; Ifkovitis et al.; Tissue Engineering; vol. 13, No. 10; Oct. 2007; pp. 2369-2385.
European Search Report mailed Jan. 12, 2015 in application No. 12186538.0.
European Search Report mailed Jun. 18, 2013 in application No. 12186536.4.
*Syntehsis and degradation of novel photocrosslinkable aromatic copolyanhydrides*; Nagata et al.; European Polymer Journal 42; Aug. 2006; pp. 2617-2622 (www.sciencedirect.com).

(Continued)

*Primary Examiner* — Ling Choi
*Assistant Examiner* — Jessica E Whiteley
(74) *Attorney, Agent, or Firm* — Renner Kenner Greive Bobak Taylor & Weber

(57) ABSTRACT

A telechelic macromer is disclosed having (meth)acrylic end-groups and a core. The macromer defined by Formula 1 comprises a core Y (Formulas 2 to 9) that is linked to (meth)acrylic groups by urethane, ester or anhydride bonds and has iodine value ranging from 5 to 75. The method involves a chemical reaction carried out in solvent, ranging 6-24 hours, wherein the precursor of a core (Formulas 2 and 3) reacts in two stages with compounds forming urethane bonds, or wherein the precursor of a core (Formulas 4 to 8) reacts in one stage with compounds forming ester bonds, or wherein the precursor of a core defined by Formula 9 reacts in one stage with compounds forming anhydride bonds. The urethane, ester and anhydride moieties comprise groups capable of free radical polymerization isolating the final product by evaporation. The composition disclosed provides the macromer, a photoinitiator and possibly a reactive diluent.

37 Claims, No Drawings

(56) References Cited

OTHER PUBLICATIONS

*Dimethacrylate Derivatives of Dimer Acid*; Trujillo-Lemon et al; Published online in Wiley InterScience (www.interscience.wiley. com); May 2006; Journal of Polymer Science; Part A: Polymer Chemistry, vol. 44; 3921-3929.
*Synthesis and characterization of telechelic macromers containing fatty acid derivatives*; El Fray et al.; Reactive & Functional Polymers 72; Jul. 31, 2012; 781-790.

* cited by examiner

TELECHELIC MACROMER, METHOD FOR PRODUCING TELECHELIC MACROMER AND COMPOSITION CONTAINING TELECHELIC MACROMER

TECHNICAL FIELD

The present invention relates to telechelic macromer susceptible to an external stimulus, a method for producing telechelic macromer susceptible to an external stimulus and a composition containing telechelic macromer. Applications of material produced from macromer include sealing packages, coatings, coating on catheters or various elements of medical equipment that are in temporary contact with living tissues.

BACKGROUND ART

Producing macromers that acquire desired physicochemical properties upon exposition to UV radiation is the subject of literature reports and numerous patents. U.S. Pat. No. 4,919,151 describes polyethers with urethane linkages synthesized in the course of reaction of polyether with isocyanate and a respective acrylate derivative. Light-sensitive systems having potential for medicine applications are reported in Nagata M., Ioka E., *Europ Polym J*, 42, 2617 (2006). They were synthesized by reaction of cinnamic acid derivative with aliphatic-aromatic hexane derivative bearing carboxylic groups. The patent application U.S. Pat. No. 6,747,088 reports a method for producing linear and branched waterborne polyurethanes that cross-link when exposed to UV light or a thermal stimulus. The multicomponent water dispersions contained protecting groups of isocyanates. These materials are applied in the production of coatings on heat-resistant surfaces. The patent application WO/1999/019003 describes gel polymer systems filled with ceramics that change their physical form at 37° C. In physiological conditions the system undergoes solidification. Preferred polymers are polysaccharides, polyamides or poly(amino acids). Light-induced cross-linking was employed in the patent application US 2009/0074868. Photo-cross-linkable cosmetic fillers comprising, for example, poly(ethylene glycol) and hyaluronic acid derivatives are reported there.

SUMMARY OF THE INVENTION

In light of the foregoing, it is a first aspect of the present invention to provide a telechelic macomer, method for producing telechelic macromer and composition containing telechelic macromer.

It is another aspect of the present invention to provide a telechelic macromer comprising (meth)acrylic end-groups and a core, wherein the macromer defined by Formula 1 comprises a core Y defined by Formulas 2 to 9 which is linked by urethane, ester or anhydride bonds to (meth)acrylic groups, and wherein the iodine value of the telechelic macromer is in the range between 5 and 75.

Yet another aspect of the present invention is to provide a method for producing telechelic macromer bearing (meth)acrylic end-groups by chemical reaction, wherein in the presence of an organic solvent and in time range of 6-24 hours the precursor of a core defined by Formulas 2 or 3 reacts in two stages with compounds forming urethane bonds, or wherein in the presence of an organic solvent and in time range of 6-24 hours the precursor of the core defined by Formulas 4 to 8 reacts in one stage with compounds forming ester bonds, or wherein in the presence of an organic solvent and in time range of 6-24 hours the precursor of the core defined by Formula 9 reacts in one stage with compounds forming anhydride bonds, wherein the urethane, ester and anhydride moieties comprise groups capable of free radical polymerization and the final product is isolated by evaporation of solvent.

Still another aspect of the present invention is to provide a composition containing telechelic macromer comprising (meth)acrylic end-groups and a core, wherein the composition comprises a macromer comprising (meth)acrylic end-groups and a core, wherein the composition comprises a macromer comprising (meth)acrylic end-groups and a core, wherein the macromer defined by Formula 1 comprises a core Y defined by Formulas 2 to 9 which is linked by urethane, ester or anhydride bonds to (meth)acrylic groups, and wherein the iodine value of the telechelic macromer is in the range between 5 and 75 and a photoinitiator.

DETAILED DESCRIPTION OF THE INVENTION

The present invention is illustrated in the following Examples and Formulas, wherein the Formulas are found at the end of the Detailed Description.

The telechelic macromer according to the present invention, comprising (meth)acrylic end-groups and a core, has a structure as shown in Formula 1 and has a core Y which is defined by Formula 2 and is defined by Formula 3 with substituents $X_1$ to $X_5$ wherein $X_1$, $X_2$, etc. can be replaced with one another to illustrate alternative sub-units of the core Y; and is linked by urethane bonds to (meth)acrylic groups. The macromer has a core defined by Formula 4 or 5 or 6 or 7 or 8 or 3 linked by ester bonds to (meth)acrylic groups. The macromer has a core defined by Formula 9 and linked by anhydride bonds to (meth)acrylic groups. The iodine value of telechelic macromer is in the range from 5 to 75.

The precursor of the core defined by Formula 2 comprises a branched dimer fatty acid compound of 36 carbon atoms per molecule, bearing primary amine end-groups (I). The amine value of the precursor is in the range of 200-210 mg KOH/g.

The macromer with a core defined by Formula 2 has urethane bonds formed by reaction of the core precursor with trimethylene carbonate or propylene carbonate and ester bonds formed by subsequent reactions with acryloyl or methacryloyl chloride.

The precursor of the core Y defined by Formula 3 comprises a branched dimer fatty acid compound of 36 carbon atoms per molecule (and then the X in Formula 3 is defined by $X_2$); or the precursor of the core Y defined by Formula 3 comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g ($X_1$); or the precursor of the core Y defined by Formula 3 is a derivative of linear aliphatic polyether or poly(ether-ester) of molar mass in the range of 600-2500 g/mol bearing hydroxyl end-groups ($X_4$ when it comprises a polyether and $X_3$ when it comprises a poly(ether or ester)); or the precursor of the core Y defined by Formula 3 is a derivative of a branched polyether compound of molar mass of 1500 g/mol, bearing hydroxyl end-groups ($X_5$).

The macromer comprising core Y defined by Formula 3 has urethane bonds formed by reactions of the precursor with 1,6-diisocyanatohexane or with 5-isocyanato-1-(isocyanatomethyl)-1,3,3-trimethylcyclohexane, or with 1,1'-methylenebis(4-isocyanatocyclohexane).

The precursor of the core Y defined by Formulas 4 or 5 comprises a branched dimer fatty acid compound of 36 carbon atoms per molecule, or the precursor of the core Y defined by Formulas 4 or 5 is a derivative of this dimer fatty acid which is the product of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g .

The precursor of the core Y-defined by Formula 6 comprises a linear aliphatic poly(ether-ester) of molar mass in the range of 600-2500 g/mol bearing hydroxyl end-groups.

The precursor of the core Y defined by Formula 7 comprises a linear aliphatic polyether of molar mass in the range of 600-2500 g/mol bearing hydroxyl end-groups.

The precursor of the core Y defined by Formula 8 comprises a branched polyether compound of molar mass of 1500 g/mol, bearing hydroxyl end-groups.

The telechelic macromer comprising a core Y defined by Formulas 4 or 5 or 6 or 7 or 8 has linking ester bonds formed by reactions of the precursor with acryloyl or methacryloyl chloride.

The precursor of the core Y defined by Formula 9 comprises a branched dimer fatty acid compound of 36 carbon atoms per molecule, or the precursor of the core Y defined by Formula 9 comprises derivatives of this dimer fatty acid which are the products of esterification of the dimer fatty acid compound with low molar mass diols of 2, 4 or 6 carbon atoms per molecule, of molar mass ranging from 570 to 3000 g/mol bearing carboxyl end-groups and its carboxyl value is in the range of 35-210 mg KOH/g.

The telechelic macromer with core Y defined by Formula 9 comprises anhydride bonds formed by reactions of the precursor with acryloyl or methacryloyl chloride.

In the method for producing telechelic macromer end-capped with (meth)acrylic groups upon chemical reaction according to the present invention, organic solvents of various polarity are used and the reaction time is in the range of 6-24 hours. The precursor of the core Y defined by Formula 2 or by Formula 3 undergoes a two-stage reaction with compounds forming urethane bonds. The precursor of the core Y defined by Formulas 4 to 8 undergoes a one-step reaction with compounds forming ester bonds. The precursor of the core Y defined by Formula 9 undergoes a one stage reaction with compounds forming anhydride bonds. The urethane, ester and anhydride moieties comprise a group that is capable of free radical polymerization and the product is isolated by solvent evaporation. The precursor of the core is dissolved in a solvent, then a proton acceptor may be added (i.e. triethylamine) and a compound that reacts with functional groups of telechelic precursor core (i.e. isocyanate, acyl chloride). This compound may comprise unsaturated bonds. After this reaction is complete, a compound comprising unsaturated bonds and end-groups capable of binding to the formerly synthesized intermediate (i.e. 2-hydroxyethyl methacrylate) may be introduced to the reaction environment. After this reaction is complete, the final product is isolated and purified.

In the method for producing the core defined by Formula 2 a precursor in the form of a branched dimer fatty acid compound of 36 carbon atoms per molecule, bearing primary amine end-groups and the amine value of said precursor is in the range of 200-210 mg KOH/g, is used.

In the method for producing the core defined by Formula 3 a precursor is used and said precursor comprises a branched dimer fatty acid compound of 36 carbon atoms per molecule (and then the X in Formula 3 is defined by $X_2$); or said precursor comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g ($X_1$); or the precursor comprises a linear aliphatic polyether or poly(ether-ester) of molar mass in the range of 600-2500 g/mol bearing hydroxyl end-groups ($X_4$ when it comprises a polyether and $X_3$ when it comprises a poly(ether or ester)); or the precursor comprises a branched polyether of molar mass of 1500 g/mol, bearing hydroxyl end-groups ($X_5$).

In the method for producing the core defined by Formulas 4 or 5 a precursor is used said precursor comprises a branched dimer fatty acid compound of 36 carbon atoms per molecule, or the precursor of the core defined by Formulas 4 or 5 comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g.

In the method for producing the core defined by Formula 6 a precursor which comprises a linear aliphatic poly(ether-ester) of molar mass in the range of 600-2500 g/mol bearing hydroxyl end-groups, is used.

In the method for producing the core defined by Formula 7 a precursor which comprises a linear aliphatic polyether of molar mass in the range of 600-2500 g/mol bearing hydroxyl end-groups, is used.

In the method for producing the core defined by Formula 8 a precursor, which comprises a branched polyether compound of molar mass of 1500 g/mol, bearing hydroxyl end-groups, is used.

In the method for producing the core defined by Formula 9 a precursor is used, and said precursor comprises a branched dimer fatty acid compound of 36 carbon atoms per molecule, or said precursor comprises derivatives of this dimer fatty acid which are the products of esterification of the dimer fatty acid compound with low molar mass diols of 2, 4 or 6 carbon atoms per molecule, of molar mass ranging from 570 to 3000 g/mol bearing carboxyl end-groups and its carboxyl value is in the range of 35-210 mg KOH/g.

Trimethylene carbonate or propylene carbonate is added to the precursor of the core defined by Formula 2 to obtain an intermediate with urethane bonds, and acryloyl or methacryloyl chloride is added and as a result linking ester bonds are formed.

1,6-diisocyanatohexane or 5-isocyanato-1-(isocyanatomethyl)-1,3,3-trimethylcyclohexane, or 1,1'-methylenebis(4-isocyanatocyclohexane) is added to the precursor of the core defined by Formula 3 to give an intermediate with urethane bonds, and 2-hydroxyethyl methacrylate (C2H4) or hydroxypropyl methacrylate (C3H6) is added and as a result linking urethane bonds are formed.

Acryloyl or methacryloyl chloride is added to the precursor of the core defined by Formulas 4 or 5 or 6 or 7 or 8 to create a macromer comprising linking ester bonds.

Acryloyl or methacryloyl chloride is added to the precursor of the core Y defined by Formula 9 to create a macromer comprising linking anhydride bonds.

In the method for producing telechelic macromer with a core Y defined by Formula 3 a reaction in methylene chloride as solvent is carried out. The first stage is carried out in the temperature range of 4-40° C. and the second stage is carried out at room temperature. The molar ratio of reactive hydroxyl and isocyanate groups in the first stage is 1:1.5 to 1:3 and in the second stage 1:1 or higher. The final product is isolated by precipitation into cold hexane and/or cold methanol, then washed with hexane and/or methanol and dried under reduced pressure.

The method for producing telechelic macromer with a core defined by Formula 3 may involve a reaction in tetrahydrofuran as solvent. The first stage is carried out in the temperature range of 4-60° C. and the second stage is carried out at room temperature. The molar ratio of reactive hydroxyl to isocyanate groups in the first stage is 1:1.5 to 1:3 and in the second stage 1:1 or higher. The final product is isolated by precipitation into cold hexane and/or cold methanol, then washed with hexane and/or methanol and dried under reduced pressure.

When methylene chloride is used as solvent for producing macromer with a core Y defined by Formula 3, a catalyst is preferably used. In the first stage the catalyst is an organic tin compound or an organic bismuth compound and in the second stage the catalyst is a tertiary cycloaliphatic amine, i.e. 1,4-diazabicyclo[2.2.2]octane or 1,8-diazabicyclo[5.4.0]undec-7-ene In the method for producing telechelic macromer with a core Y defined by Formula 2 the first stage is carried out in the temperature range of 20-40° C., wherein the molar ratio of carbonate compound to amine compound is at least 1:1. The telechelic intermediate bearing urethane bonds obtained after the first stage has hydroxyl value of 140-160 mg KOH/g. In the second stage this intermediate undergoes a reaction carried out in an organic solvent, i.e. methylene chloride, in the presence of triethylamine and at the temperature range of 4-20° C. Preferably, after the reaction is complete, the reaction mixture is washed with saturated sodium bicarbonate, after that it is washed with deionized water and washed with brine. The organic layer is dried over anhydrous magnesium sulphate and the solvent is evaporated under reduced pressure.

The method for producing telechelic macromer with core Y defined by Formulas 4 or 5 or 6 or 7 or 8 or 9 involves a reaction in methylene chloride as solvent. The reaction is carried out in the temperature range of 4-20° C., in the presence of triethylamine. The acylating agent is used in excess. Preferably, the reaction mixture is washed with saturated sodium bicarbonate, after that it is washed with deionized water and washed with brine. The organic layer is dried over anhydrous magnesium sulphate and the solvent is evaporated under reduced pressure.

According to the present invention, the composition containing telechelic macromer contains said telechelic macromer comprising a core and end-capped with (meth)acrylic groups and a photoinitiator The photoinitiator is introduced to the macromer with the help of a solvent which dissolves both the macromer and the initiator in an extent that enables obtaining the desired amount of the initiator in the composition. The photoinitiator content is in the range of 0.5-2% with respect to the total weight of the composition.

Preferably, the photoinitiator is a compound that comprises an aromatic ring in the position $\alpha$ to a carbonyl group, possibly substituents at the aromatic ring or phosphine oxide group and the photoinitiator is used in the amount of 0.5-2% with respect to the total weight of the composition. For example, 2-hydroxy-1-[4-(2-hydroxyethoxy)phenyl]-2-methyl-1-propanone or 2,2-Dimethoxy-2-phenylacetophenone or phenylbis(2,4,6-trimethylbenzoyl)phosphine oxide may be used.

The composition comprises a reactive diluent, poly(ethylene glycol) diacrylate of molar mass in the range of 250-700. The weight ratio of total macromer and photoinitiator to the diluent varies from 1:99 to 99:1.

The composition comprises a reactive diluent, trimethylolpropane triacrylate or tri(propylene glycol) diacrylate or ethoxylated trimethylolpropane triacrylate. The weight ratio of total macromer and photoinitiator to the diluent varies from 1:99 to 99:1. The composition comprising one or more of the three said diluents may, additionally, comprise poly(ethylene glycol) diacrylate of molar mass in the range of 250-700 g/mol at weight ratio from 1:99 to 99:1 with respect to the total macromer, photoinitiator and other said diluents.

Compositions containing telechelic macromers according to the present invention are capable of undergoing transition from liquid or waxy state to a solid upon UV radiation of low intensity. The obtained macromers are derivatives of fatty acids, of polyethers and of poly(ether-ester)s and comprise linking anhydride, ester and urethane groups. Molar mass of the obtained macromers is below 15 000 g/mol (by GPC) and their iodine value is not greater than 75 (by Wijs method). The macromers comprise groups capable of intermolecular hydrogen bonding. These groups include, but are not limited to, urethane groups.

The advantage of the present invention is that the telechelic macromers comprise ester, anhydride and urethane bonds that link the core to end-groups capable of free radical polymerization. Materials of this kind may be easily shaped at room temperature and acquire desired properties of a solid upon exposition to an external stimulus—UV light of low intensity. The macromers and compositions may be enriched with fillers which include, but are not limited to: bioactive glass, alginate microcapsules, hydroxyapatite or starch powder.

The following Examples illustrate methods for producing telechelic macromers and compositions containing telechelic macromers. The Figures illustrate chemical Formulas of telechelic macromer. Formula 1 represents telechelic macromer; Formula 2 represents a core of telechelic macromer comprising urethane and ester bonds; Formula 3 represents a core of telechelic macromer comprising urethane and/or ester and/or ether bonds and substituents $X_n$ and R, wherein $X_1$, $X_2$, etc can be replaced with one another to illustrate alternative sub-units of the core Y; Formula 4 represents a core of telechelic macromer comprising ester bonds; Formula 5 represents a core of another telechelic macromer comprising ester bonds; Formula 6 represents a core of another telechelic macromer comprising ester bonds; Formula 7 represents a core of another telechelic macromer comprising ester bonds; Formula 8 represents a core of another telechelic macromer comprising ester bonds; and Formula 9 represents a core of telechelic macromer comprising anhydride, and possibly ester, bonds. Methods for producing telechelic macromers are given in Examples 1-10. Methods of producing composition comprising telechelic macromer and methods of its crosslinking are given in Examples 11-14.

EXAMPLES

Example I

One weight equivalent of saturated a,w-dicarboxy derivative of dimer fatty acid of 36 carbon atoms per molecule and carboxyl value of 196 mg KOH/g and 0.44 weight equivalents of dry triethylamine are added to dry methylene chloride cooled down to 4° C. The reaction vessel is flushed with inert gas. The mixture is stirred for 30 minutes and 0.43 weight equivalents of methacryloyl chloride are added, while maintaining the reaction temperature under 5° C. After all chloride has been added, the reaction is continued at room temperature. The progress of the reaction is followed by thin layer chromatography (the mobile phase is a mixture of methylene chloride with hexane). After the reaction is complete, the precipitate is filtered off. The filtrate is then washed with saturated sodium bicarbonate (twice), with deionized water (twice) and with brine (once) and the organic layer is then dried over anhydrous magnesium sulphate. A small amount of phenothiazine is then added and the solvent is evaporated under reduced pressure. In the final stage of solvent removal the product is precipitated into anhydrous diethyl ether which is then evaporated under reduced pressure. The solvent is evaporated in the temperature range of 10-40° C. The final product is a viscous, dark yellow liquid.

The telechelic macromer features the following properties:
$^1$H NMR: 0.72-1.71 ppm (m, 68H), 1.97 (s, 6H), 2.50 ppm (t, 4H), 5.79 ppm (s, 2H), 6.18 ppm (s, 2H), 6.65-7.15 ppm (m, br)

molar mass $M_n$=2800 g/mol, dispersity index DI=1.22 (GPC, solutions in THF, computed against polystyrene standards of $M_n$ 523000, 204000, 96000, 20235, and 7200).

iodine value IV=49.0

Example II

The reaction is carried out in a way analogous to Example I. One weight equivalent of poly[di(ethylene glycol)adipate] of $M_n$=2500 g/mol, 0.1 weight equivalents of dry triethylamine and 0.08 weight equivalents of acryloyl chloride are used. The whole process is carried out in a way analogous to Example I.

The telechelic macromer features the following properties:
1H NMR: 1.65 ppm (m, 52H), 2.34 ppm (t, 54H), 3.67 ppm (t, 54H), 4.21 ppm (t, 54H), 5.84 ppm (m, 2H), 6.14 ppm (m, 2H), 6.41 ppm (m, 2H)

iodine value IV=19.0

Example III

The reaction is carried out in a way analogous to Example I. One weight equivalent of poly(ethylene glycol) of degree of polymerization equal to 14, 0.42 weight equivalents of dry triethylamine and 0.39 weight equivalents of methacryloyl chloride are used. The whole process is carried out in a way analogous to Example I.

The telechelic macromer features the following properties:
$^1$H NMR: 1.94 ppm (s, 6H), 3.56 ppm (m, 50H), 3.63 ppm (t, 4H), 4.24 (t, 4H), 5.51 ppm (s, 2H), 6.10 ppm (s, 2H)

iodine value IV=59.0

Example IV

The reaction is carried out in a way analogous to Example I. One weight equivalent of branched poly(1,3-propanediol) of $M_n$=1500 g/mol, 0.24 weight equivalents of dry triethylamine and 0.21 weight equivalents of acryloyl chloride are used. The whole process is carried out in a way analogous to Example I.

The telechelic macromer features the following properties:
$^1$H NMR: 1.65-1.83 ppm (m, 48H), 3.30 ppm (t, 3H), 3.35-3.54 ppm (m, 94H), 3.88 ppm (m, 1H), 4.13 ppm (t, 6H), 5.85 ppm (m, 3H), 6.14 ppm (m, 3H), 6.40 ppm (m, 3H)

iodine value IV=26.7

Example V

All reactions are carried out in methylene chloride at a temperatures range from 4 to 40° C. One weight equivalent of saturated α,ω-diamine derivative of branched dimer fatty acid of amine value of 205 mg KOH/g is introduced into a round bottom flask and 0.42 weight equivalents of trimethylene are added. The reaction is continued until the infrared band characteristic for cyclic carbonate ring decays completely. The product is washed with diethyl ether and its hydroxyl number is determined. In the second stage this intermediate undergoes a reaction with methacryloyl chloride in the amount sufficient to ensure that all hydroxyl groups are consumed. The second stage and purification of the product is carried out in a way analogous to the process described in Example I.

The telechelic macromer features the following properties:
$^1$H NMR: 0.7-1.7 ppm (m, 72H), 1.94 ppm (s, 6H), 2.01 ppm (m, 4H), 3.15 ppm (t, 4H), 4.16 ppm (t, 4H), 4.25 ppm (t, 4H), 4.67 ppm (br, 2H), 5.56 ppm (s, 2H), 6.10 ppm (s, 2H)

molar mass $M_n$=1200 g/mol, dispersity index DI=1.09 (GPC, solutions in THF, computed against polystyrene standards of $M_n$ 523000, 204000, 96000, 20235, and 7200).

iodine value IV=58.1

Example VI

The reaction is carried out in a way analogous to Example I. One weight equivalent of oligoesterdiol which is a product of reaction of the dimer fatty acid referred to in Example I with low molar mass diol and has hydroxyl value of approximately 56 mg KOH/g, 0.15 weight equivalents of dry triethylamine and 0.13 weight equivalents of methacryloyl chloride are used. The whole process is carried out in a way analogous to Example I.

The telechelic macromer features the following properties:
$^1$H NMR: 0.7-1.8 ppm (m, 200H), 1.94 (s, 6H), 2.28 ppm (t, 12H), 2.53 (s, br), 4.05 ppm (t, 12H), 4.14 (t, 4H), 5.54 ppm (m, 2H), 6.09 ppm (m, 2H)

molar mass $M_n$=6000 g/mol, dispersity index DI=1.37 (GPC, solutions in THF, computed against polystyrene standards of $M_n$ 523000, 204000, 96000, 20235, and 7200)

iodine value IV=23.8

Example VII

The reaction is carried out in a way analogous to Example I. One weight equivalent of branched dimer fatty acid derivative of hydroxyl value of 205 mg KOH/g, 0.44 weight equivalents of dry triethylamine and 0.4 weight equivalents of methacryloyl chloride are used. The whole process is carried out in a way analogous to Example I.

The telechelic macromer features the following properties:
$^1$H NMR: 0.7-1.8 ppm (m, 68H), 1.94 (s, 6H), 2.28 ppm (t, 12H), 2.53 (s, br), 4.13 ppm (t, 4H), 5.53 ppm (m, 2H), 6.09 ppm (m, 2H)

molar mass $M_n$=1000 g/mol, dispersity index DI=1.05 (GPC, solutions in THF, computed against polystyrene standards of $M_n$ 523000, 204000, 96000, 20235, and 7200)

iodine value IV=74.2

Example VIII

The reaction is carried out in a round bottom flask equipped with a reflux condenser. 0.23 weight equivalents of isophorone diisocyanate (5-isocyanato-1-(isocyanatomethyl)-1,3,3-trimethylcyclohexane) are dissolved in dry methylene chloride and a small amount of dibutyltin dilaurate is added. Solution of the oligoesterdiol described in Example VI in methylene chloride is now added stepwise to the reaction mixture. The amount of the oligoesterdiol is one weight equivalent. After the whole volume of the solution has been added, the temperature is raised to 40° C. The first stage of the reaction is considered complete when two consecutive n-butyldiamine based determinations of isocyanate groups give same result. A small amount of phenothiazine is then added, and subsequently 0.13 weight equivalents of 2-hydroxyethyl methacrylate and 1,4-diazabicyclo[2.2.2]octane are introduced into the flask. The reaction is continued until infrared spectroscopy or titration in the presence of n-butyldiamine shows no isocyanate groups left in the system. After the reaction is complete, part of the solvent is removed under reduced pressure and the product is precipitated into cold methanol. The product is then several times thoroughly washed with methanol and warm deionized water, for example at the temperature 40-50° C. and is dried under reduced pressure at room temperature.

The telechelic macromer features the following properties:
$^1$H NMR: 0.7-1.8 ppm (m, 228H), 1.94 (s, 6H), 1.96 (m, 2H), 2.28 ppm (t, 12H), 2.53 ppm (br, 4H), 2.92 i 3.29 ppm (br,4H), 3.78 ppm (br, 2H), 4.05 ppm (t, 12H), 4.31 ppm (m, br, 12H), 4.4-4.9 ppm (vbr, 4H), 5.54 ppm (s, 2H), 6.09 ppm (s, 2H)

molar mass=12500 g/mol, dispersity index DI=1.21 (GPC, solutions in THF, computed against polystyrene standards of $M_n$ 523000, 204000, 96000, 20235, and 7200)
iodine value IV=10.5

Example IX

The reaction is carried out in a round bottom flask equipped with a reflux condenser. 0.14 weight equivalents of 1,6-diisocyanatohexane are dissolved in dry methylene chloride and a small amount of bismuth (III) n-hexanoate is added. Solution of poly[di(ethylene glycol) adipate] of $M_n$=2500 g/mol in methylene chloride is now added stepwise to the reaction mixture. The amount of poly[di(ethylene glycol) adipate] is one weight equivalent. After the whole volume of the solution has been added, the temperature is raised to 60° C. The first stage of the reaction is considered complete when two consecutive n-butyldiamine based determinations of isocyanate groups give same result. A small amount of phenothiazine is then added, and subsequently 0.12 weight equivalents of 2-hydroxyethyl methacrylate are introduced into the flask. The reaction is continued until infrared spectroscopy or titration in the presence of n-butyldiamine shows no isocyanate groups left in the system. After the reaction is complete, part of the solvent is removed under reduced pressure and the product is precipitated into cold hexane. The product is then several times thoroughly washed with warm hexane, for example at the temperature 30-40° C. and is dried under reduced pressure at room temperature.

The telechelic macromer features the following properties:
$^1$H NMR: 1.31 ppm (m, 8H), 1.47 ppm (m, 8H), 1.65 ppm (m, 48H), 1.93 ppm (s, 6H), 2.34 ppm (t, 48H), 3.15 ppm (t, 8H), 3.67 ppm (t, 48H), 4.21 ppm (t, 48H), 4.29 ppm (t, 8H), 4.87 (br, 4H), 5.57 ppm (s, 2H), 6.11 ppm (s, 2H).

molar mass $M_n$=7900 g/mol, dispersity index DI=1.82 (GPC, solutions in THF, computed against polystyrene standards of $M_n$ 523000, 204000, 96000, 20235, and 7200)
iodine value IV=8.2

Example X

The process is carried out in a way analogous to Example IX. 0.36 weight equivalents of 1,1'-methylenebis(4-isocyanatocyclohexane), 1 weight equivalent of branched poly(1,3-propanediol) of $M_n$=1500 g/mol and 0.18 weight equivalents of 2-hydroxyethyl methacrylate are used.

The telechelic macromer features the following properties:
$^1$H NMR: 1.15-1.89 ppm (m, 88H), 1.94 ppm (s, 6H), 3.35-3.50 ppm (m, 94H), 3.56-3.71 (m, 5H), 3.88 ppm (m, 1H), 4.22 ppm (t, 4H), 4.29 ppm (m, 8H), 4.50-4.82 ppm (br, 4H), 5.58 ppm (s, 2H), 6.13 ppm (s, 2H).
iodine value IV=11.4

Example XI 0.04 g of a photoinitiator in the form of 2-hydroxy-1-[4-(2-hydroxyethoxy)phenyl]-2-methyl-1-propanone is dissolved in 1 ml of chloroform. This solution is added to a vial containing 2 ml of chloroform and 2 g of the macromer from Example VIII. After a homogenous solution has been formed, it is poured into mould and the solvent is evaporated under reduced pressure. The process of solvent removal is gravimetrically controlled. After the solvent has been removed completely, the remained viscous liquid is irradiated with UV/Vis light of wavelength above 280 nm and intensity of 10 mW/cm$^2$ for 200 seconds. As a result the composition is cross-linked and an elastic film is obtained.

The elastic film features the following properties:
gel fraction (in methylene chloride): GF=0.25
glass transition: −49° C. (at heating from −90° C., 10 K/min)
tensile strength: 2950 kPa
elongation at break: 150%

Example XII 0.05 g of a photoinitiator in the form of phenylbis(2,4,6-trimethylbenzoyl)phosphine is dissolved in 2 ml of chloroform. This solution is added to a vial containing 8 ml of chloroform and 4 g of the product from Example IX. After a homogenous solution is formed, it is poured into mould and the solvent is evaporated under reduced pressure. The process of solvent removal is gravimetrically controlled. After the solvent has been fully removed, the remained viscous liquid is irradiated with UV/Vis light of wavelength above 280 nm and intensity of 10 mW/cm$^2$ for 100 seconds. As a result the composition is cross-linked and an elastic film is obtained.

The elastic film features the following properties:
gel fraction (in methylene chloride): GF=0.92
glass transition: −53° C.
tensile strength: 1200 kPa
elongation at break: 70%

Example XIII 0.05 g of a photoinitiator in the form of phenylbis(2,4,6-trimethylbenzoyl)phosphine is dissolved in 1 g of reactive diluent, poly(ethylene glycol) diacrylate of molar mass of 700 g/mol. Afterwards, 1.5 g of the product from Example V is added to the mixture. The viscous liquid is irradiated with UV/V is light of wavelength above 280 nm and intensity of 20 mW/cm$^2$ for 100 seconds. As a result the composition is cross-linked and an elastic film is obtained.

The elastic film features the following properties:
gel fraction (in methylene chloride): GF=0.85
glass transition: 45° C. (at heating from −90°, 10 K/min)

Example XIV 0.03 g of a photoinitiator in the form of phenylbis(2,4,6-trimethylbenzoyl)phosphine is dissolved in 1.5 g of reactive diluent, tri(propylene glycol) diacrylate. Afterwards, 1.5 g of the product from Example VIII is added to the mixture. The viscous liquid is irradiated with UV/V is light of wavelength above 280 nm and intensity of 20 mW/cm$^2$ for 100 seconds. As a result the composition is cross-linked and an elastic film is obtained.

The elastic film features the following properties:
gel fraction (in methylene chloride): GF=0.69
glass transition: 103° C. (at heating from −90° C., 10 K/min)

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

Formulas

Formula 1

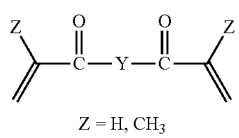

$Z = H, CH_3$

Formula 2

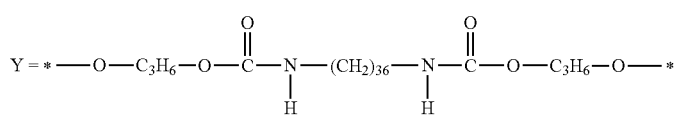

Formula 3

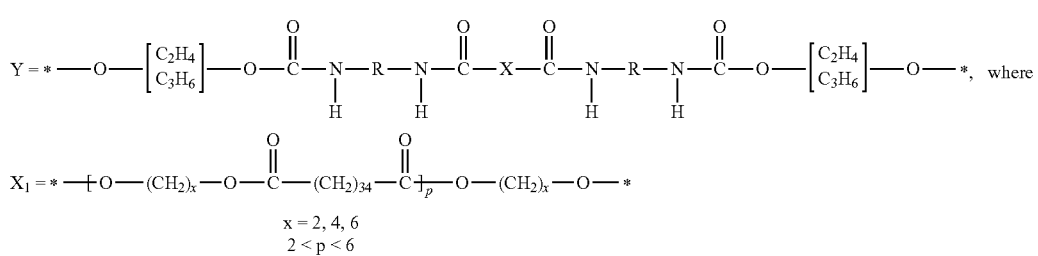, where

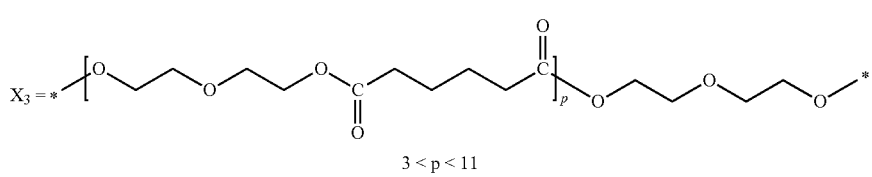

$x = 2, 4, 6$
$2 < p < 6$

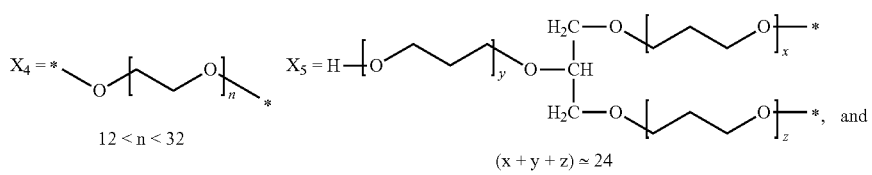

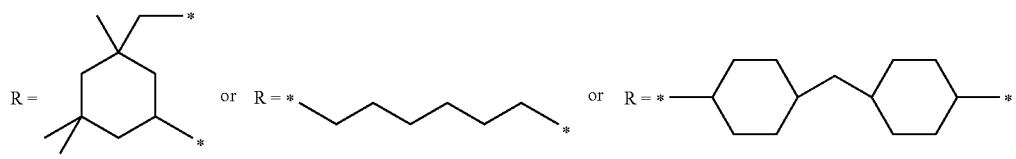

$3 < p < 11$

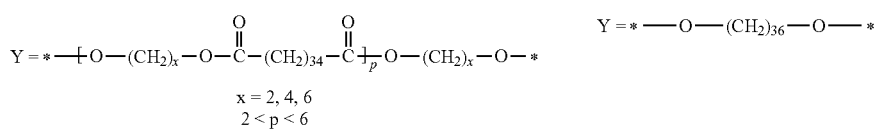

$12 < n < 32$     $(x + y + z) \simeq 24$, and

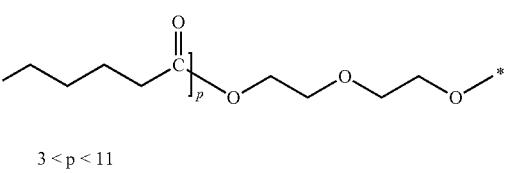

Formula 4

$Y = * -\!\!\left[O-(CH_2)_x-O-\overset{O}{\underset{\|}{C}}-(CH_2)_{34}-\overset{O}{\underset{\|}{C}}\right]_p\!\!-O-(CH_2)_x-O-*$ $x = 2, 4, 6$
$2 < p < 6$ Formula 5

$Y = * -O-(CH_2)_{36}-O-*$

Formula 6

$Y = * -\left[O\diagdown\!\!\diagup O\diagdown\!\!\diagup O-\overset{O}{\underset{\|}{C}}-\!\!\diagdown\!\!\diagup\!\!\diagdown\!\!-\overset{O}{\underset{\|}{C}}\right]_p\!\!-O\diagdown\!\!\diagup O\diagdown\!\!\diagup O-*$ $3 < p < 11$ -continued Formula 7

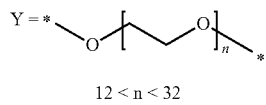

$12 < n < 32$

Formula 8

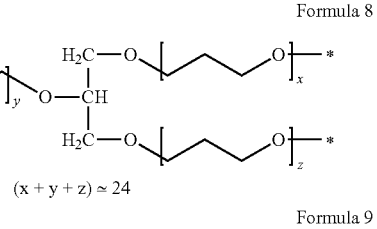

$(x + y + z) \simeq 24$

Formula 9

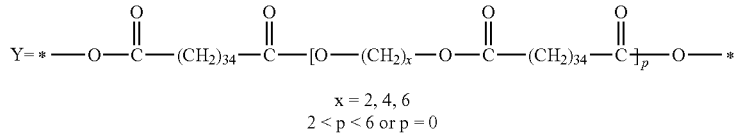

$x = 2, 4, 6$
$2 < p < 6 \text{ or } p = 0$

What is claimed is:

1. A telechelic macromer comprising (meth)acrylic end-groups and a core, wherein the macromer defined by Formula 1

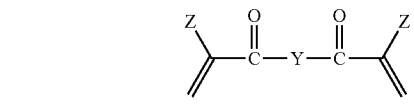

$Z = H, CH_3$ comprising a core Y defined by a formula selected from the group consisting of Formulas 2 to 9

Formula 2

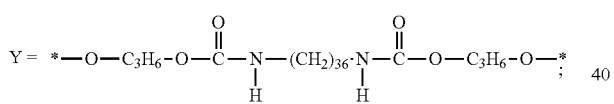

Formula 3

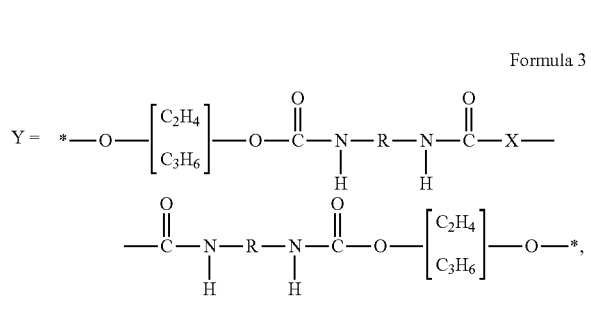

where X is selected from formulas of $X_1$, $X_2$, $X_3$, $X_4$ and $X_5$, wherein

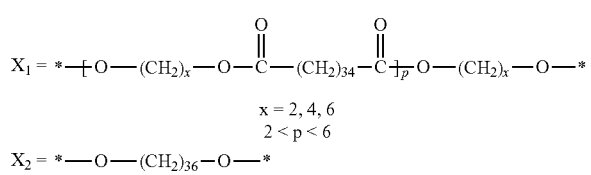

$x = 2, 4, 6$
$2 < p < 6$

-continued

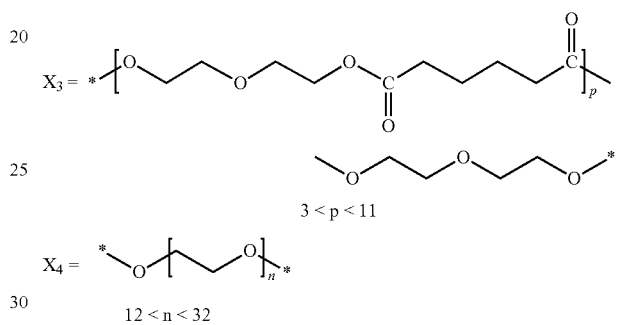

$3 < p < 11$ $12 < n < 32$ and R is selected from

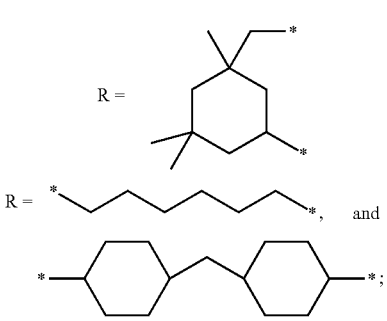

Formula 5

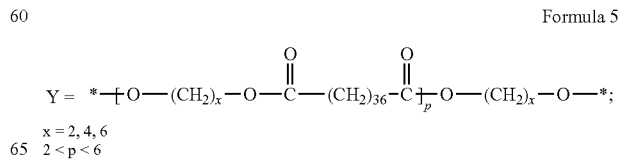

$x = 2, 4, 6$
$2 < p < 6$

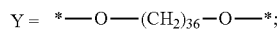

Formula 6

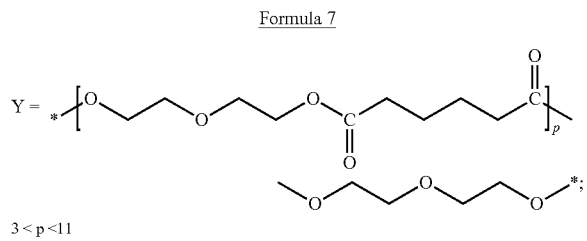

Formula 7

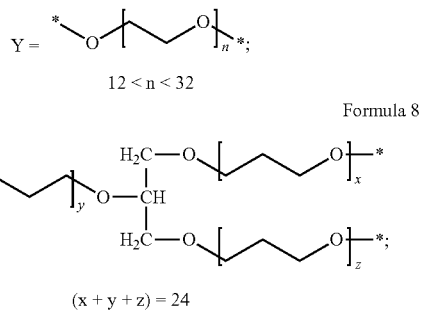

Formula 8

And

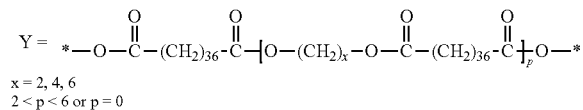

Formula 9 which is linked by urethane, ester or anhydride bonds to (meth)acrylic groups, and wherein the iodine value of the telechelic macromer is in the range between 5 and 75.

2. A telechelic macromer according to claim 1, wherein the precursor of the core defined by Formula 2 comprises a branched dimer fatty acid compound of 36 carbon atoms per molecule and comprises primary amine end-groups, and said precursor has amine value of 200-210 mg KOH/g.

3. A telechelic macromer according to claim 2, wherein the urethane bonds are formed by reaction of the core precursor with trimethylene carbonate or propylene carbonate and the linking ester bonds are formed by subsequent reactions with (meth)acryloyl chloride.

4. A telechelic macromer according to claim 1, wherein the precursor of the core defined by Formula 3 comprises a branched dimer fatty acid compound of 36 carbon atoms per molecule or it comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and its hydroxyl value is in the range of 50-210 mg KOH/g or wherein the precursor of the core defined by Formula 3 comprises a linear aliphatic polyether or poly(ether-ester) of molar mass in the range of 600-2500 g/mol bearing hydroxyl end-groups or wherein the precursor of the core defined by Formula 3 comprises a branched polyether compound of molar mass of 1500 g/mol, bearing hydroxyl end-groups.

5. A telechelic macromer according to claim 4, wherein the linking urethane bonds are formed by reaction of the core precursor with 1,6-diisocyanatohexane or with 5-isocyanato-1-(isocyanatomethyl)-1,3,3-trimethylcyclohexane, or with 1,1'-methylenebis(4-isocyanatocyclohexane).

6. A telechelic macromer according to claim 1, wherein the precursor of the core defined by Formulas 4 or 5 comprises a branched dimer fatty acid compound of 36 carbon atoms per molecule or it comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and the hydroxyl value of said precursor is in the range of 50-210 mg KOH/g.

7. A telechelic macromer according to claim 1, wherein the precursor of the core defined by Formula 6 comprises linear aliphatic poly(ether-ester) of molar mass in the range of 600-2500 g/mol bearing hydroxyl end-groups.

8. A telechelic macromer according to claim 1, wherein the precursor of the core defined by Formula 7 comprises linear polyether of molar mass in the range of 600-2500 g/mol bearing hydroxyl end-groups.

9. A telechelic macromer according to claim 1, wherein the precursor of the core defined by Formula 8 comprises branched polyether of molar mass of 1500 g/mol bearing hydroxyl end-groups.

10. A telechelic macromer according to claim 6 or 7 or 8 or 9, wherein the linking ester bonds are formed by reaction of the core precursor with (meth)acryloyl chloride.

11. A telechelic macromer according to claim 1, wherein precursor of the core defined by Formula 9 comprises branched dimer fatty acid compound of 36 carbon atoms per molecule, or it comprises derivatives of this dimer fatty acid which are the products of esterification of the dimer fatty acid compound with low molar mass diols of 2, 4 or 6 carbon atoms per molecule, of molar mass ranging from 570 to 3000 g/mol bearing carboxyl end-groups and the carboxyl value of said precursor is in the range of 35-210 mg KOH/g.

12. A telechelic macromer according to claim 11, wherein the linking anhydride bonds are formed by reaction of the core precursor with (meth)acryloyl chloride.

13. A method for producing the telechelic macrmomer of claim 1 (meth)acrylic end-groups by chemical reaction, wherein in the presence of an organic solvent and in time range of 6-24 hours the precursor of a core defined by Formulas 2 or 3 reacts in two stages with compounds forming urethane bonds, or wherein in the presence of an organic solvent and in time range of 6-24 hours the precursor of the core defined by Formulas 4 to 8 reacts in one stage with compounds forming ester bonds, or wherein in the presence of an organic solvent and in time range of 6-24 hours the precursor of the core defined by Formula 9 reacts in one stage with compounds forming anhydride bonds, wherein the urethane, ester and anhydride moieties comprise groups capable of free radical polymerization and the final product is isolated by evaporation of solvent.

14. A method according to claim 13, wherein a core defined by Formula 2 is produced from a precursor which comprises branched dimer fatty acid compound of 36 carbon atoms per molecule, bearing primary amine end-groups and which has amine value in the range of 200-210 mg KOH/g.

15. A method according to claim 13, wherein a core defined by Formula 3 is produced from a precursor which comprises a branched dimer fatty acid compound of 36 carbon atoms per molecule or it comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and which has hydroxyl value in the range of 50-210 mg KOH/g, or wherein the core defined by Formula 3 is produced from a precursor which comprises a linear aliphatic polyether or poly(ether-ester) of molar mass in the range of 600-2500 g/mol bearing hydroxyl end-groups, or wherein the core defined by Formula 3 is produced from precursor which comprises branched polyether compound of molar mass of 1500 g/mol, bearing hydroxyl end-groups.

16. A method according to claim 13, wherein a core defined by Formulas 4 and 5 is produced from a precursor which comprises a branched dimer fatty acid compound of 36 carbon atoms per molecule or it comprises derivatives of this dimer fatty acid which are the products of esterification of the dimer fatty acid compound with low molar mass diols of 2, 4 or 6 carbon atoms per molecule, of molar mass ranging from 540 to 2000 g/mol bearing hydroxyl end-groups and which has hydroxyl value in the range of 50-210 mg KOH/g.

17. A method according to claim 13, wherein a core defined by Formula 6 is produced from a precursor which comprises a linear aliphatic poly(ether-ester) of molar mass in the range of 600-2500 g/mol bearing hydroxyl end-groups.

18. A method according to claim 13, wherein a core defined by Formula 7 is produced from a precursor which comprises a linear aliphatic polyether of molar mass in the range of 600-2500 g/mol bearing hydroxyl end-groups.

19. A method according to claim 13, wherein a core defined by Formula 8 is produced from a precursor which comprises a branched polyether of molar mass of 1500 g/mol bearing hydroxyl end-groups.

20. A method according to claim 13, wherein a core defined by Formula 9 is produced from a precursor which comprises a branched dimer fatty acid compound of 36 carbon atoms per molecule or from precursor which comprises derivatives of this dimer fatty acid which are the products of esterification of the dimer fatty acid compound with low molar mass diols of 2, 4 or 6 carbon atoms per molecule, of molar mass ranging from 570 to 3000 g/mol bearing carboxyl end-groups and which has carboxyl value in the range of 35-210 mg KOH/g.

21. A method according to claim 14, wherein upon adding trimethylene or propylene carbonate an intermediate comprising urethane bonds is produced and wherein upon adding (meth)acryloyl chloride a macromer comprising linking ester bonds is produced.

22. A method according to claim 15, wherein 1,6-diisocyanatohexane or 5-isocyanato-1-(isocyanatomethyl)-1,3,3-trimethylcyclohexane, or 1,1'-methylenebis(4-isocyanatocyclohexane) is added, thus producing a macromer comprising urethane bonds.

23. A method according to claim 22, wherein 2-hydroxyethyl methacrylate or hydroxypropyl methacrylate is added.

24. A method according to claim 16 or 17 or 18 or 19, wherein (meth)acryloyl chloride is added, thus producing a macromer comprising linking ester bonds.

25. A method according to claim 20, wherein (meth)acryloyl chloride is added, thus producing a macromer comprising linking anhydride bonds.

26. A method according to claim 15, wherein the reaction is carried out in methylene chloride, and wherein the first stage is carried out in the temperature range of 4-40° C. and the second stage is carried out at room temperature, and wherein the OH:NCO molar ratio in the first stage is between 1:1.5 and 1:3 and in the second stage 1:1 or higher, and wherein the final product is precipitated into cold hexane and/or cold methanol, washed with methanol and/or hexane and dried under reduced pressure.

27. A method according to claim 15, wherein the reaction is carried out in tetrahydrofuran as an organic solvent, and wherein the first stage is carried out in the temperature range of 4-60° C. and the second stage is carried out at room temperature, and wherein the OH:NCO molar ratio in the first stage is between 1:1.5 and 1:3 and in the second stage 1:1 or higher, and wherein the final product is precipitated into cold hexane and/or cold methanol, washed with methanol and/or hexane and dried under reduced pressure.

28. A method according to claim 26 or 27, wherein a catalyst is added; the catalyst used in the first stage is an organic tin or bismuth compound and the catalyst used in the second stage is a tertiary cycloaliphatic amine, i.e. 1,4-diazabicyclo[2.2.2]octane or 1,8-diazabicyclo[5.4.0]undec-7-ene.

29. A method according to claim 21, wherein the first stage is carried out in the temperature range of 20-40° C., and wherein the carbonate:amine molar ratio equals 1:1 or higher and an intermediate of hydroxyl value of 140-160 mg KOH/g comprising urethane is produced, and wherein the second stage is carried out in methylene chloride in the temperature range of 4-20° C. in the presence of triethylamine, and wherein the final product is isolated by washing with saturated sodium bicarbonate, followed by washing with deionized water and washing with brine, and followed by drying the organic layer over anhydrous magnesium sulphate and followed by removal of the solvent under reduced pressure.

30. A method according to claim 24, wherein methylene chloride is used as an organic solvent, and wherein the acylating agent is used in excess and the reaction is carried out in the temperature range of 4-20° C. in the presence of triethylamine.

31. A method according to claim 25, wherein methylene chloride is used as an organic solvent, and wherein the acylating agent is used in excess and the reaction is carried out in the temperature range of 4-20° C. in the presence of triethylamine.

32. A method according to claim 30, wherein when the reaction is complete the reaction mixture is washed with saturated sodium bicarbonate, washed with deionized water and washed with brine, and afterwards the organic layer is dried over anhydrous magnesium sulphate and the solvent is removed under reduced pressure.

33. A method according to claim 31, wherein when the reaction is complete the reaction mixture is washed with saturated sodium bicarbonate, washed with deionized water and washed with brine, and afterwards the organic layer is dried over anhydrous magnesium sulphate and the solvent is removed under reduced pressure.

34. A composition containing telechelic macromer comprising (meth)acrylic end-groups and a core, wherein the composition comprises a macromer according to claim 1 and a photoinitiator.

35. A composition according to claim 34, wherein the photoinitiator compound comprises an aromatic ring in position α to a carbonyl group, possibly substituents at the aromatic ring and possibly a phosphine oxide group, and wherein the photoinitiator is used in the amount of 0.5-2 weight %.

36. A composition according to claim 34, wherein the composition comprises a reactive diluent which is poly(ethylene glycol) diacrylate of molar mass in the range of 250 to 700 g/mol, and wherein the weight content of the reactive diluent in the composition varies from 1:99 to 99:1.

37. A composition according to claim 34, wherein the composition comprises a reactive diluent which is trimethylolpropane triacrylate or tri(propylene glycol) diacrylate or ethoxylated trimethylolpropane triacrylate, and wherein the weight content of the reactive diluent in the composition varies from 1:99 to 99:1.

* * * * *